United States Patent [19]
Horner et al.

[11] Patent Number: 6,012,825
[45] Date of Patent: Jan. 11, 2000

[54] DEFECT HIGHLIGHTING LUMINAIRE AND INSPECTION AREA

[75] Inventors: Terrence V. Horner, North York; Chas Latter, Etobicoke, both of Canada

[73] Assignee: Lighting Dimensions, Etobicoke, Canada

[21] Appl. No.: 08/922,059

[22] Filed: Sep. 2, 1997

[51] Int. Cl.[7] .................................................. F21K 27/00
[52] U.S. Cl. .......................... 362/260; 362/219; 362/296; 362/297; 362/298
[58] Field of Search .................................. 362/217, 219, 362/260, 296, 301, 138, 297, 298, 300, 302, 225; 356/237.2, 239.7

[56] References Cited

U.S. PATENT DOCUMENTS 2,845,854  8/1958  Kurek ....................................... 362/260
5,436,726  7/1995  Ventura et al. .......................... 356/371

*Primary Examiner*—Nimeshkumar D. Patel
*Assistant Examiner*—Michael J. Smith
*Attorney, Agent, or Firm*—Connolly Bove Lodge & Hutz LLP

[57] ABSTRACT

A luminaire to illuminate an article to be visually inspected for surface defects includes a housing having an opening in a forward face thereof. At least one elongate light source is accommodated by the housing. At least one linear reflector is also accommodated by the housing. The at least one linear reflector has at least one forwardly directed, angled reflective surface that directs light emitted by the at least one elongate light source such that the luminaire projects light onto a specular surface of an article being inspected resulting in a plurality of laterally, spaced images of the at least one elongate light source being reflected by the specular surface.

26 Claims, 9 Drawing Sheets

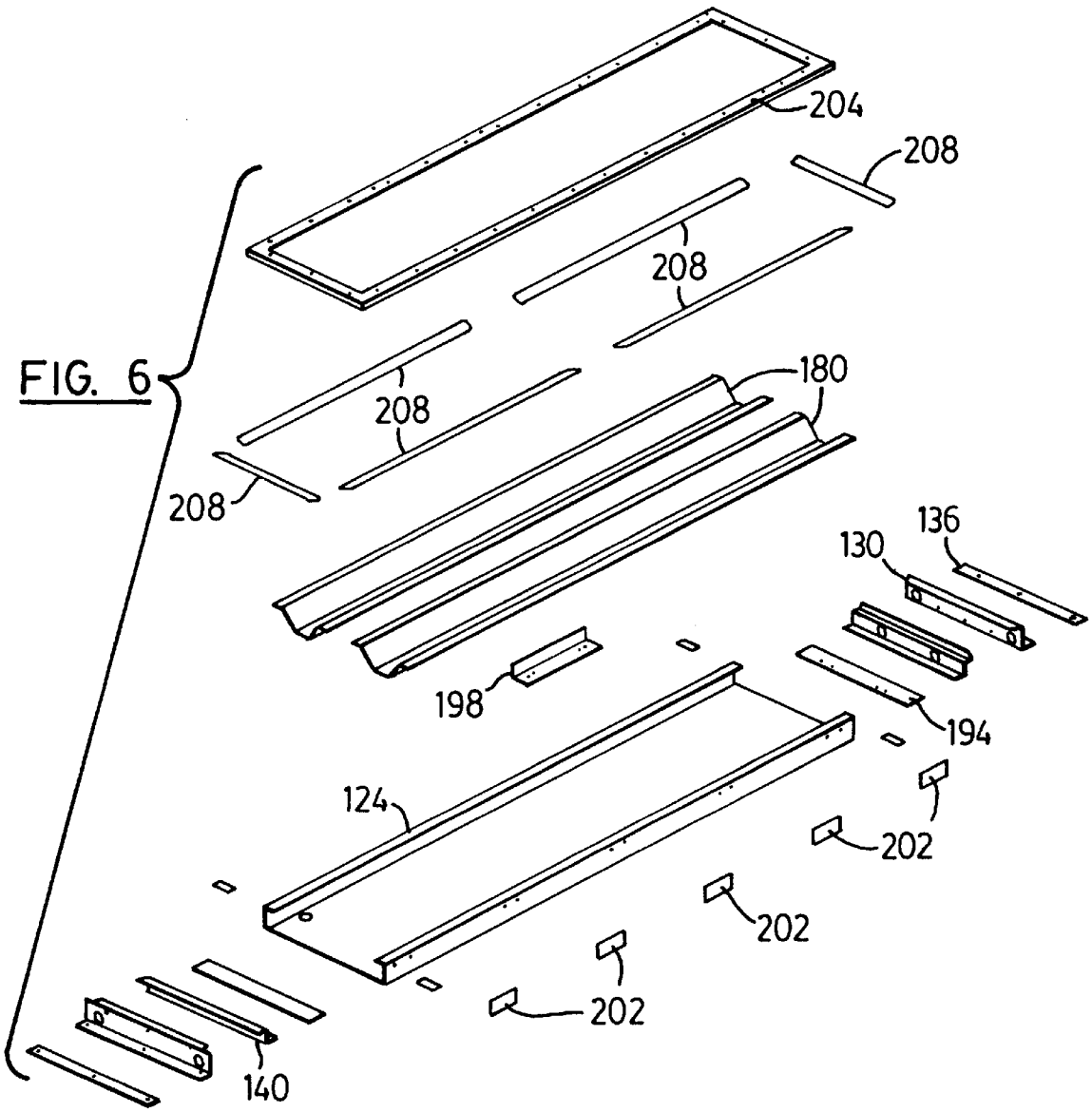

DEFECT HIGHLIGHTING LUMINAIRE AND INSPECTION AREA

FIELD OF THE INVENTION

The present invention relates to article inspection and in particular to an inspection area and a luminaire for the same to facilitate the visual inspection of coated articles for surface defects.

BACKGROUND OF THE INVENTION

In many manufacturing environments, it is necessary to visually inspect articles being assembled to detect surface defects. In the automotive industry, inspection areas are located along the assembly line so that assembled automobiles can be inspected for surface defects such as for example dirt, sags, dents, dings, fisheyes, scratches, mottle, orange peel etc.

To facilitate visual inspection of the automobile coated surfaces, the inspection areas include rows of fluorescent luminaires installed above and/or on opposite sides of the assembly line. The luminaires are equipped with various types of fluorescent lamps including high output (HO) or very high output (VHO) fluorescent lamps. As the automobiles travel along the assembly line and pass through the inspection area they are illuminated and the images of luminaire lenses and fluorescent lamps are reflected by the specular surfaces. The recommended illumination is at least 200 foot-candles (fd). In many instances the illumination is well above this level.

Inspection personnel detect defects by viewing the specular surfaces from various angles depending on the relative position of the reflected images and the position of inspection personnel. Arranging conventional luminaires to achieve the desired illuminance creates many problems. In particular, the illuminance level results in discomfort and disability glare causing inspection personnel to suffer eye fatigue, headaches and/or migraines. Also, inspection personnel must constantly bob and weave to see visual defects in the distorted luminaire lens images reflected by the specular surfaces thereby increasing the risk of back pain.

To reduce glare, baked enamel high reflectance reflectors with prismatic lenses have been used in the luminaires. Unfortunately, the images reflected by these luminaires onto the specular surfaces of the automobiles being inspected include images of the reflectors and lenses with images of the fluorescent lamps superimposed thereon. The resulting reflected images are distorted and unclear making it more difficult for inspection personnel to detect surface defects.

Specular lenses have also been used in luminaires with clear lenses and without lenses in the luminaire. Although the reflected images are apparent they are not sharp due to contamination which rapidly decreases reflectivity resulting in blurred images. As well, the highly specular reflective material tends to bend and flex easily resulting in distortion of the reflected images and creating secondary vague images.

In addition to the above problems, conventional luminaries have typically consumed significant amounts of power, much of which is converted into heat. This heat dissipation has resulted in an increase in fluorescent lamp temperature which reduces the light output of the fluorescent lamp. As will be appreciated, improved luminaires for facilitating the visual inspection of articles to detect surface defects are desired.

It is therefore an object of the present invention to provide a novel inspection area and a luminaire for the same.

SUMMARY OF THE INVENTION

According to one aspect of the present invention there is provided a luminaire to illuminate an article to be visually inspected comprising:

a housing having an opening in a face thereof;

at least one elongate light source accommodated by said housing; and at least one linear reflector within said housing and having at least one forwardly directed, angled reflective surface, said at least one reflective surface directing light emitted by said at least one elongate light source so that said luminaire projects through said opening, light to illuminate a specular surface of said article being inspected resulting in a plurality of laterally spaced images of said at least one elongate light source being reflected by said specular surface.

Preferably, the luminaire includes at least a pair of laterally spaced elongate fluorescent lamp assemblies and a pair of linear reflectors associated with each of the fluorescent lamp assemblies. The linear reflectors of each pair are located on opposite sides of the associated fluorescent lamp assembly.

In a preferred embodiment, the linear reflectors of each pair are mounted on a rigid support to reflect the straight edges of the fluorescent lamps with minimal distortion. The support includes a pair of diverging, forwardly extending panels on opposed sides of the associated fluorescent lamp bridged by an intermediate panel directly behind the fluorescent lamp. The diverging panels form angles with the intermediate panels equal to about 130 degrees. Thus, in the case where the luminaire includes a pair of fluorescent lamp assemblies, six laterally spaced, distinct fluorescent lamp images are reflected by the specular surface of the article being inspected when illuminated.

According to another aspect of the present invention there is provided a luminaire to illuminate an article to be visually inspected comprising:

a generally rectangular housing having an opening in a forward face thereof;

a pair of laterally spaced fluorescent lamp assemblies within said housing, each fluorescent lamp assembly including an elongate fluorescent lamp; and a pair of linear reflectors within said housing associated with each fluorescent lamp assembly, the linear reflectors of each pair being located on opposite sides of said associated fluorescent lamp assembly and presenting angled, forwardly directed reflective surfaces, said reflective surfaces directing light emitted by said fluorescent lamp assemblies so that said luminaire projects light through said opening to illuminate a specular surface of said article being inspected resulting in a plurality of laterally spaced images of each fluorescent lamp being reflected by said specular surface.

According to yet another aspect of the present invention there is provided an inspection area for an assembly line including a plurality of luminaires, said luminaires being positioned relative to said assembly line to illuminate specular surfaces of articles traveling along said assembly line, at least one of said luminaires comprising:

a housing having an opening in a face thereof;

at least one fluorescent lamp assembly accommodated by said housing and including an elongate fluorescent lamp; and at least one linear reflector within said housing and having at least one forwardly directed, angled reflective surface, said at least one reflective surface directing light emitted by said at least one fluorescent lamp assembly so that said luminaire projects through said opening, light to illuminate a specular surface of said article being inspected resulting in a plurality of laterally spaced images of said at least one fluorescent lamp being reflected by said specular surface.

In still yet another aspect of the present invention there is provided a method of visually inspecting articles to detect surface defects comprising the steps of:

projecting light onto a specular surface of an article being inspected which results in a plurality of laterally spaced images of at least one elongate light source being reflected by said specular surface;

moving the projected light relative to said specular surface; and detecting distortions in said reflected images thereby to detect surface defects.

The present invention provides advantages in that the luminaire projects light onto the article being inspected such that repetitive, laterally spaced elongate light source images are reflected by specular surfaces of the article being inspected. Defects in the specular surfaces of the articles distort the reflected elongate light source images as the articles move relative to the luminaires. Since the reflected elongate light source images are repetitive, distinct and clear, distortions in the reflected elongate light source images are easily noticed thereby facilitating surface defect detection. Also, the present invention provides advantages in that glare, veiling and power consumption are reduced while maintaining illuminance at recommended levels.

BRIEF DESCRIPTION OF THE DRAWINGS

Embodiments of the present invention will now be described more fully with reference to the accompanying drawings in which:

FIG. 6 is an exploded perspective view of the luminaire of FIG. 5;

DETAILED DESCRIPTION OF THE PREFERRED EMBODIMENT

Figure 1:
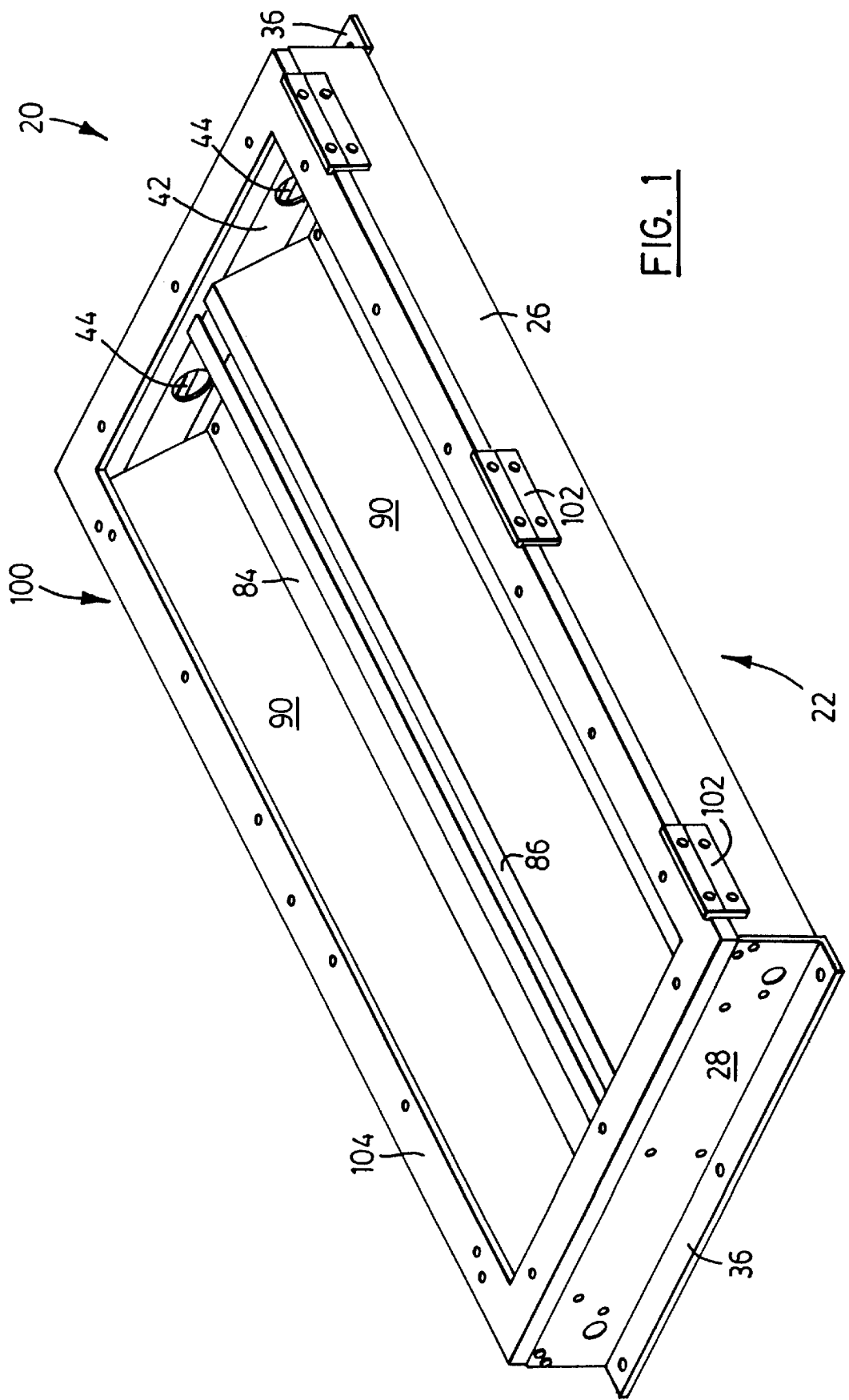
FIG. 1 is a perspective view of a luminaire for use in an automobile assembly line inspection area in accordance with the present invention.
Figure 2:
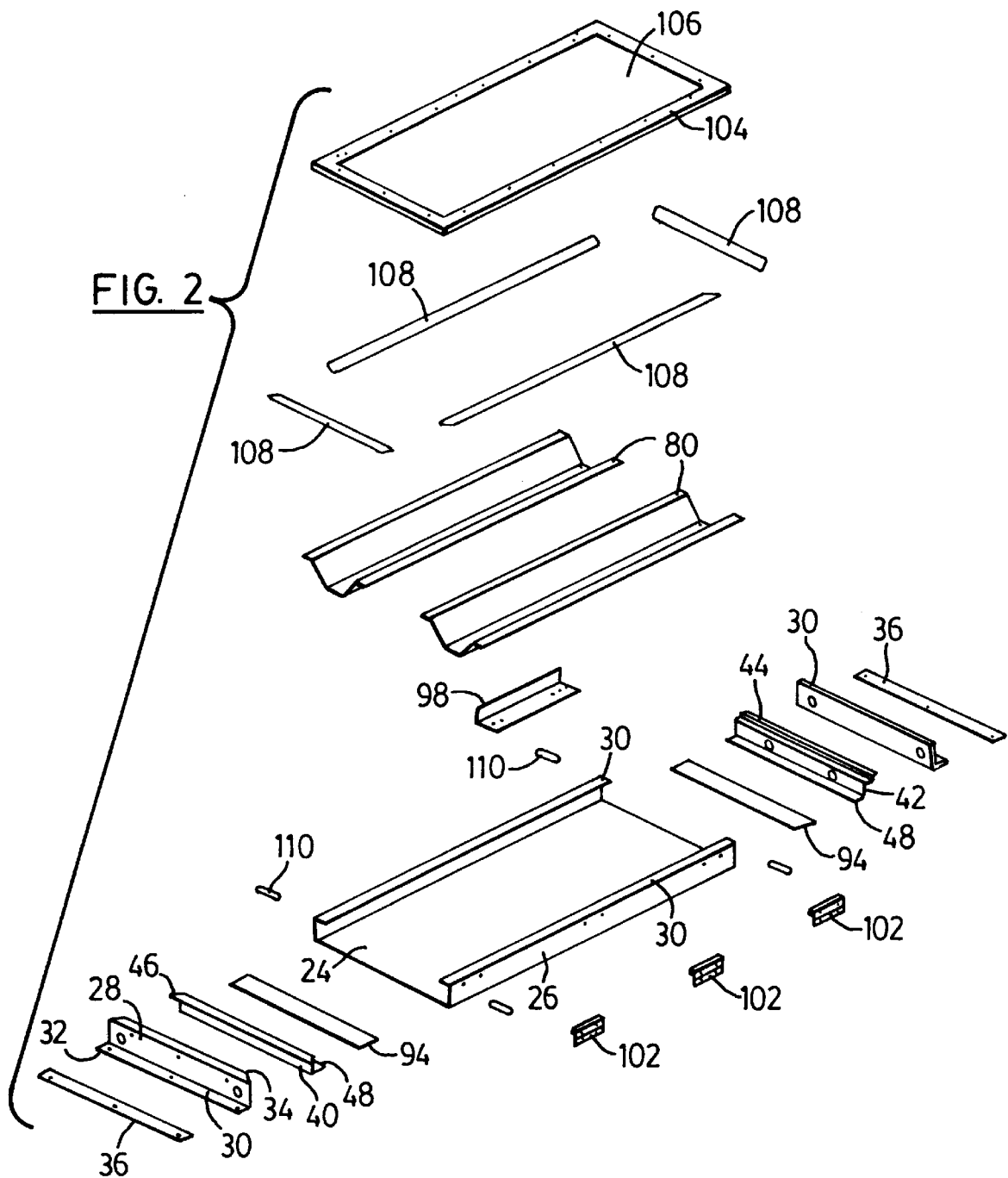
FIG. 2 is an exploded perspective view of the luminaire of FIG. 1.
Figure 3:
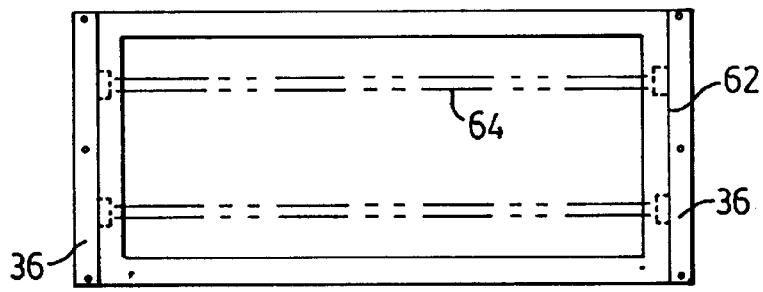
FIG. 3 is a top plan view of the luminaire of FIG. 1.
Figure 7:
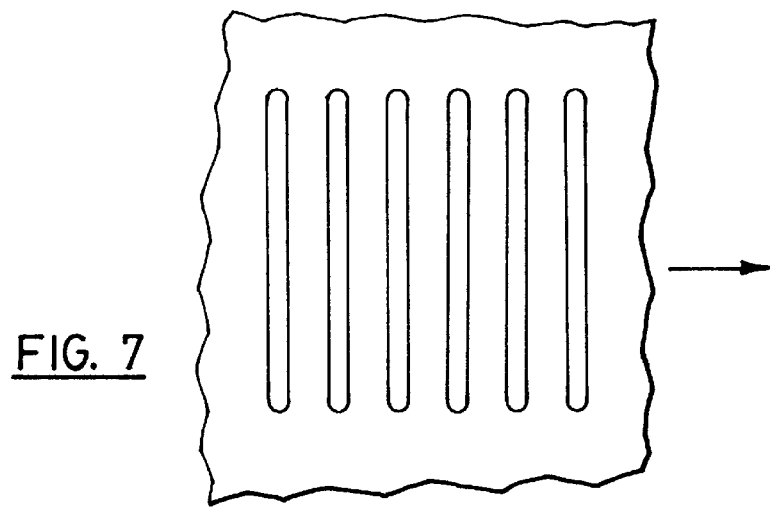
FIG. 7 is a plan view of a specular surface reflecting images of fluorescent lamps when illuminated by one of the luminaires of FIGS. 1 and 5.
Figure 4A:
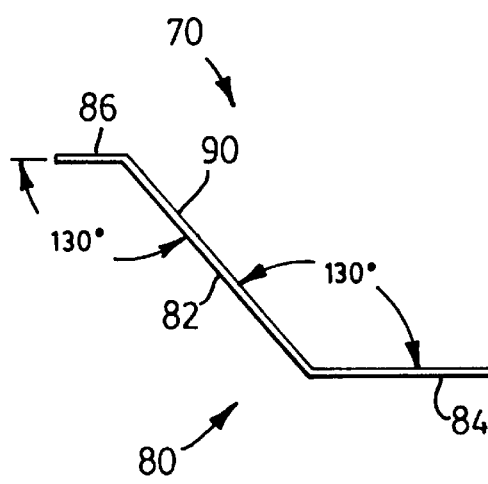
FIGS. 4a and 4b are front elevational and perspective views respectively of a reflector forming part of the luminaire of FIG. 1.
Figure 4B:
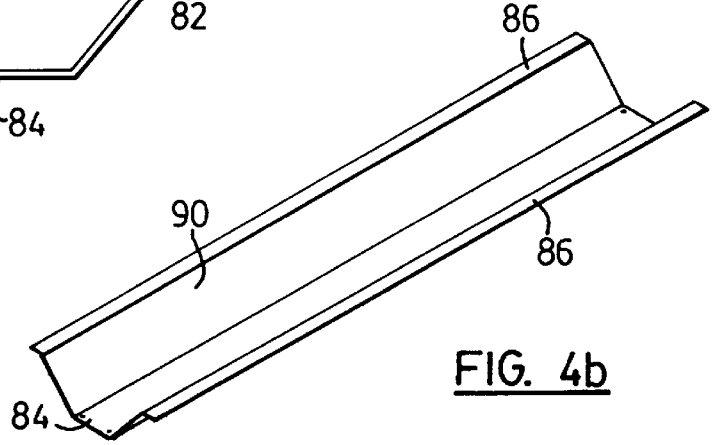

Referring now to FIGS. 1 to 3, a luminaire for use in an inspection area is shown and is generally indicated to by reference numeral 20. The luminaire 20 projects light onto specular surfaces of articles being inspected resulting in a plurality of laterally spaced, elongate fluorescent lamp images being reflected by the specular surfaces. As the articles and luminaire are moved relative to one another, inspection personnel examine the reflected fluorescent lamp images to detect and locate surface defects such as for example, dirt, sags, dents, dings, fisheyes, scratches, mottle, orange peel, etc. Surface defects are detected when the defects pass through sharp linear edges of the reflected fluorescent lamp images which results in distortion of the reflected fluorescent lamp images.

As can be seen, luminaire 20 includes a generally rectangular housing 22 having a base 24, a pair of opposed side walls 26 and a pair of opposed end walls 28. The side walls 26 are integrally formed with the base 24. Flanges 29 extend inwardly from the upper peripheral edges of the side walls 26. The end walls 28 are defined by end plates 30 secured to the base 24 by fasteners (not shown) so that the end walls 28 remain flush with the side walls 26 and base 24. Each end plate 30 has an outwardly directed flange 32 formed along its bottom peripheral edge and an inwardly directed flange 34 formed along its upper peripheral edge. Secured to the flanges 32 by way of fasteners (not shown) are support mounting brackets 36 to accommodate suspension wires or fasteners to allow the luminaire 20 either to be hung from or fastened to a support surface.

Within the housing 22 and secured to the flange 34 of each end plate 30 is a socket bracket 40. Each socket bracket 40 includes a main panel 42 having a pair of spaced apertures 44 therein. Flanges 46 and 48 extend outwardly in opposite directions from the upper and lower peripheral edges of the panel 42. The upper flange 46 overlies the inwardly directed flange 34 on the end plate 30 and is secured to it by fasteners (not shown).

Also within the housing 22 are a pair of laterally spaced, fluorescent lamp assemblies. Each fluorescent lamp assembly includes a pair of terminals 62 adjacent opposite ends of the housing and an energy efficient, low wattage fluorescent lamp 64 such as for example a T8 or T12 fluorescent lamp extending between the terminals 62. Preferably, the fluorescent lamps 64 provide illuminance equal to about 200 F.C. and use daylight phosphors in the range of about 5000 to 6500 Kelvin (K) at 72 to 85 Colour Rendering Index (CRI). The terminals 62 are positioned in the spaces between the socket brackets 40 and the end plates 30 and are in-line with the apertures 44 in the socket brackets.

Behind each fluorescent lamp 64 is a highly polished, linear specular reflector assembly 70. Each linear specular reflector assembly 70 includes a rigid sheet steel support 80 including a pair of diverging forwardly extending panels 82 bridged by an intermediate panel 84. Each diverging panel 82 forms an angle with the intermediate panel 84 equal to approximately 130 degrees. Flanges 86 extend from the peripheral edges of the diverging panels 82 and are parallel with the plane of the intermediate panel 84.

Linear reflectors 90 formed of thin, highly specular aluminum are provided on the diverging panels 82. The linear reflectors 90 in the present example are 0.016" thick and have a reflectance equal to approximately 93%. The linear reflectors 90 are secured to the diverging panels 82 via sheet adhesive in a manner so that the linear reflectors remain flat to reflect the straight edges of the fluorescent lamps with minimum distortion. The intermediate panels 84 are finished in a black matte enamel to inhibit ghost reflections from the fluorescent lamps 64 and thereby reduce distortion. Opposed ends of the supports 80 are secured to mounting brackets 94 by way of fasteners (not shown) passing through holes in the intermediate panels 84. The mounting brackets 94 are fastened to the lower flanges 48 of the socket brackets 40 by way of fasteners (not shown).

A ballast (not shown) is also provided in the housing 22 and is electrically connected to the pairs of terminals 62. The ballast may be either of the magnetic or electronic type. Better energy savings are achieved when using an electronic ballast with T8 fluorescent lamps. A power cable or power cord set (not shown) extends into the housing 22 and is connected the ballast. The ballast is mounted on a bracket 98 secured to the base 24 and positioned between the linear reflector assemblies 70.

A door 100 covers the open forward face of the housing 22 and is pivotally connected to the housing 22 by way of a plurality of hinges 102. The door 100 is retained in a closed position by releasable fasteners (not shown) located at spaced locations along one side of the housing 22 to seal the housing and inhibit dirt from contacting the linear reflectors which will decrease the efficiency of the linear reflectors 90 resulting in blurred fluorescent lamp images and a loss of illuminance. When the fasteners are released, the door 100 is pivotable to an open position to permit access to the interior of the housing 22. The door 100 includes a rectangular frame 104 surrounding and supporting a tempered glass lens 106. The glass lens 106 is sealed to the frame 104 by way of a sealing gasket (not shown) and galvanized steel retainers 108.

Metal bridges 110 are riveted in place at each end of the base 24 so as to close the space at each corner where the door 100 and end plate 30 come in contact, thereby providing a continuous surface for contacting the sealing gasket.

The orientation of the diverging panels 82 relative to the intermediate panels 84 helps to reduce glare and veiling. Also, the spacing of the fluorescent lamps 64 and the volume of the housing 22 results in heat being distributed generally evenly throughout the housing maintaining a relatively constant internal temperature therein. By maintaining a relatively constant temperature in the housing, the efficiency and lifetime of the fluorescent lamps 64 are increased.

When the fluorescent lamps 64 of the luminaire 20 are illuminated, the forwardly directed linear reflectors 90 on the diverging panels 82 reflect light emitted by the fluorescent lamps 64 with little distortion and project images of the fluorescent lamps 64 through the lens 106. Thus, in the present case, each linear reflector 90 projects an image of a fluorescent lamp 64 so that the luminaire 20 projects six (6) laterally spaced images of the fluorescent lamps. The angles of the linear reflectors 90 relative to the intermediate panels 84 ensure that fluorescent lamp images projected by the linear reflectors 90 are spaced sufficiently to avoid fluorescent lamp image overlap when reflected by the specular surfaces. Although the linear reflectors 90 are described as forming angles with the intermediate panels 84 equal to about 130 degrees, other angles can be selected to suit inspection personnel preference while avoiding fluorescent lamp image overlap.

Figure 5:
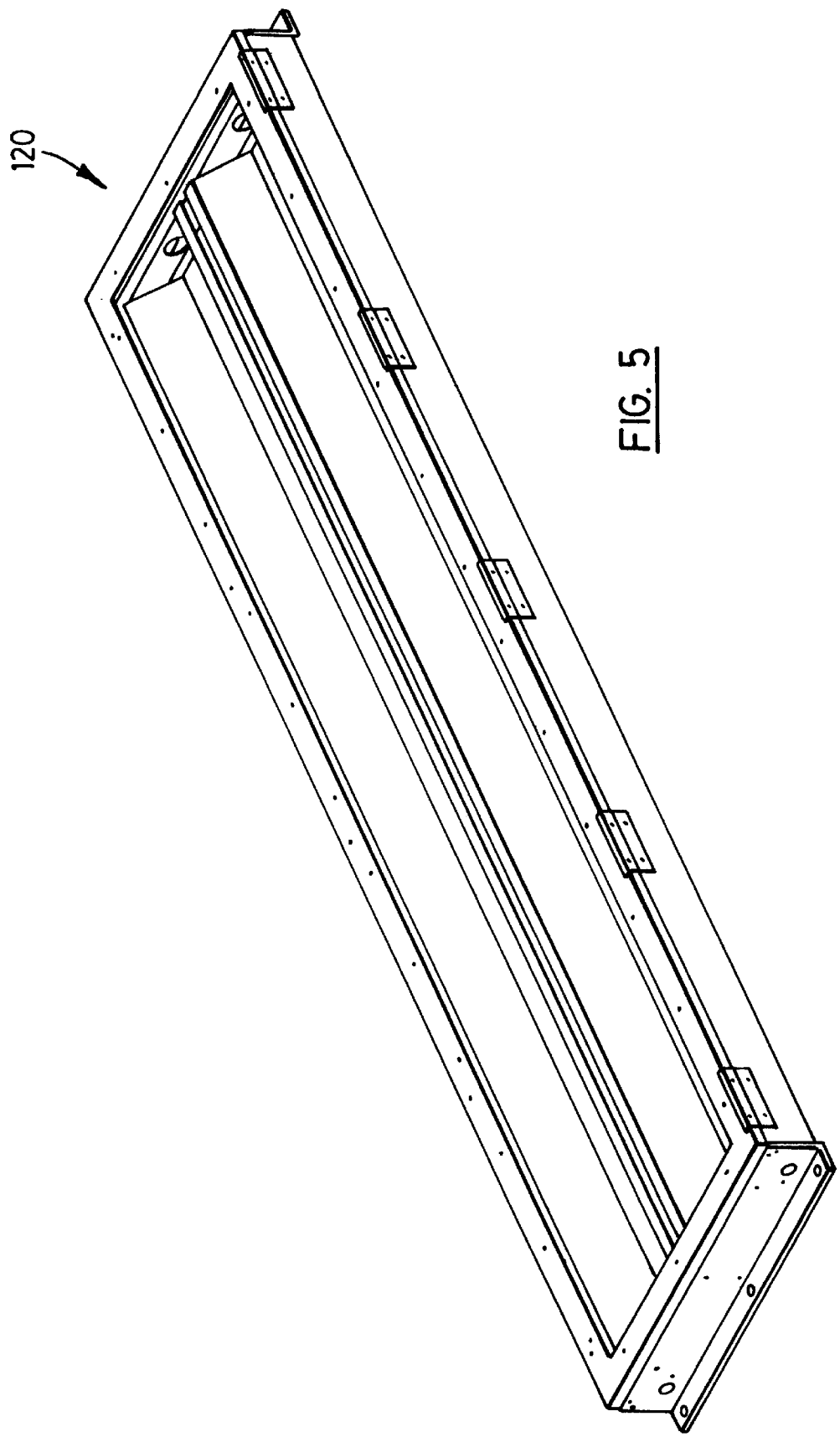
FIG. 5 is a perspective view of another embodiment of a luminaire in accordance with the present invention.

FIGS. 5 and 6 illustrate another embodiment of a luminaire 120. In this embodiment, like reference numerals are used to indicate like components of the previous embodiment with a "100" added for clarity. As can be seen, the luminaire 22 is basically the same as the luminaire 20 except that its dimensions are larger.

The luminaires 20 and 120 are particularly useful for facilitating surface defect detection in specular surfaces of automobiles. When an automobile passes through an inspection area including luminaires 20 and 120, the luminaires 20 and 120 illuminate all of the specular surfaces of the automobile visible to inspection personnel so that inspection personnel can visually inspect the specular surfaces. Each luminaire projects light onto the specular surface resulting in six (6) laterally spaced images of fluorescent lamps being reflected by the specular surfaces. The reflected repetitive fluorescent lamp images have sharp linear edges of demarcation and are clearly visible to the inspection personnel. Surface defects in the specular surfaces cause distortions in the sharp edges of the reflected fluorescent lamp images which are easily noticed by inspection personnel. As the automobile travels past the luminaires, the inspection personnel can follow the distortions through the sharp edges of reflected fluorescent lamp images allowing the inspection personnel to locate and correct the surface defects.

Referring now to FIGS. 8a to 8d, embodiments of automobile assembly line inspection areas including luminaires of the types shown in FIGS. 1 and 5 are illustrated. As can be seen, in the inspection area 200 of FIG. 8a, a pair of luminaires 220 are suspended from a ceiling surface 202 by way of suspension wires 204 and are angled with respect to the ceiling surface. In this case, the assembly line 206 is close to ground level.

Figure 8A:
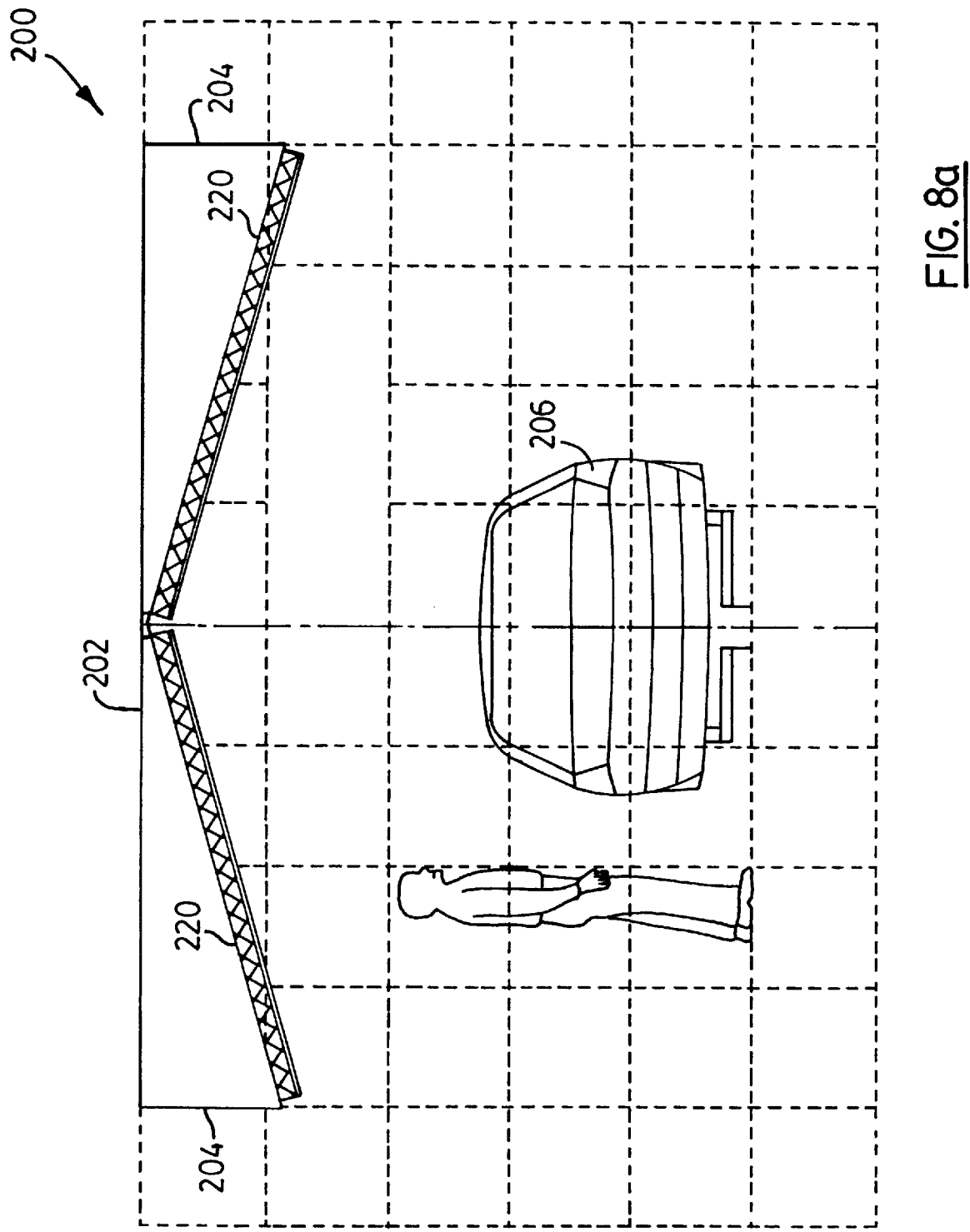
FIGS. 8a to 8d show embodiments of automobile assembly line inspection areas including the luminaires of FIG. 1 and 5.
Figure 8B:
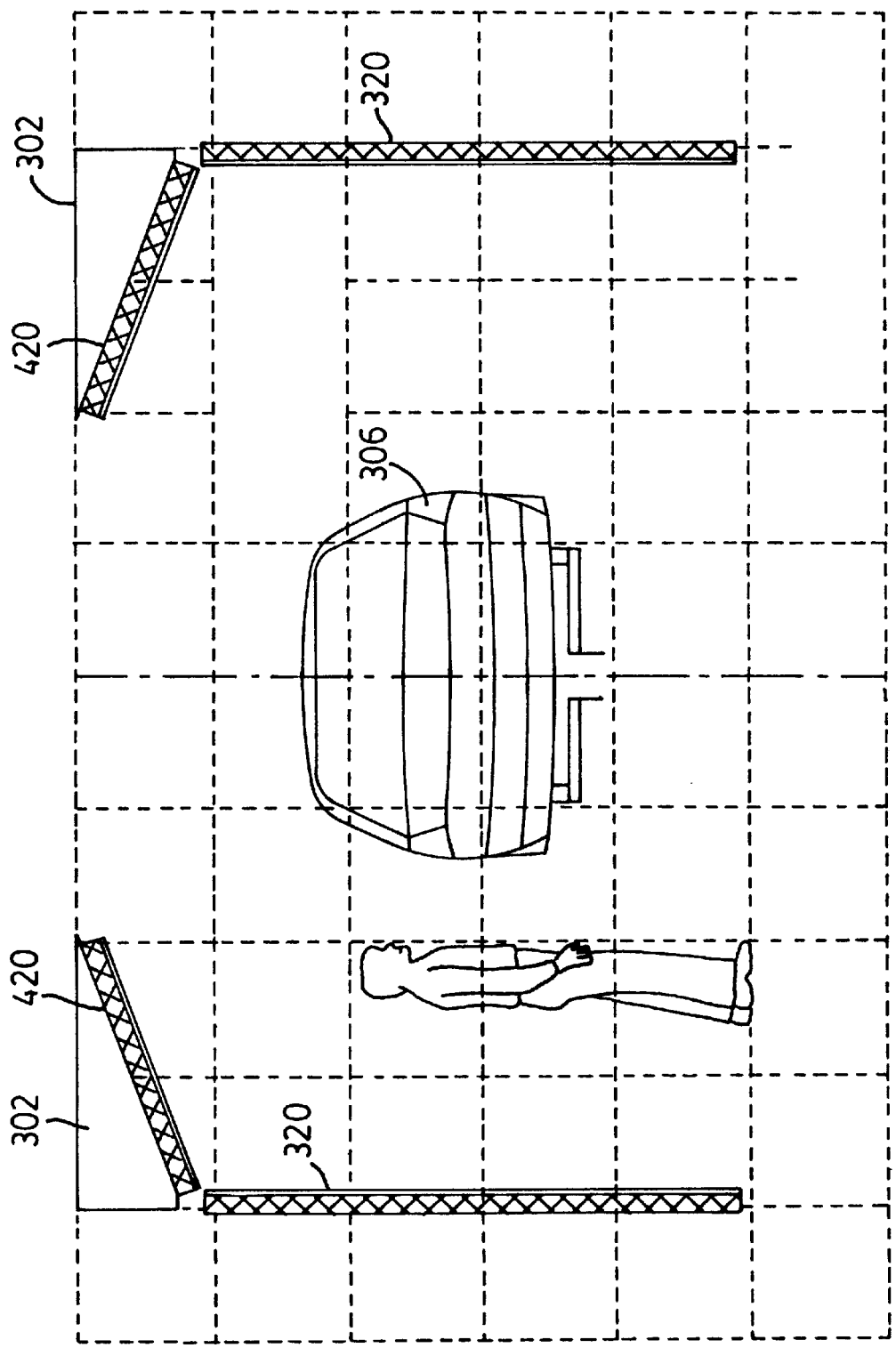

In the embodiment of FIG. 8b, large upright luminaires 320 are provided on opposite sides of the assembly line 306. Smaller luminaires 420 are suspended from the ceiling surface 302 and form a 20 degree angle with respect to the ceiling surface. In this case, the assembly line 306 is generally at waist level with respect to inspection personnel.

Figure 8C:
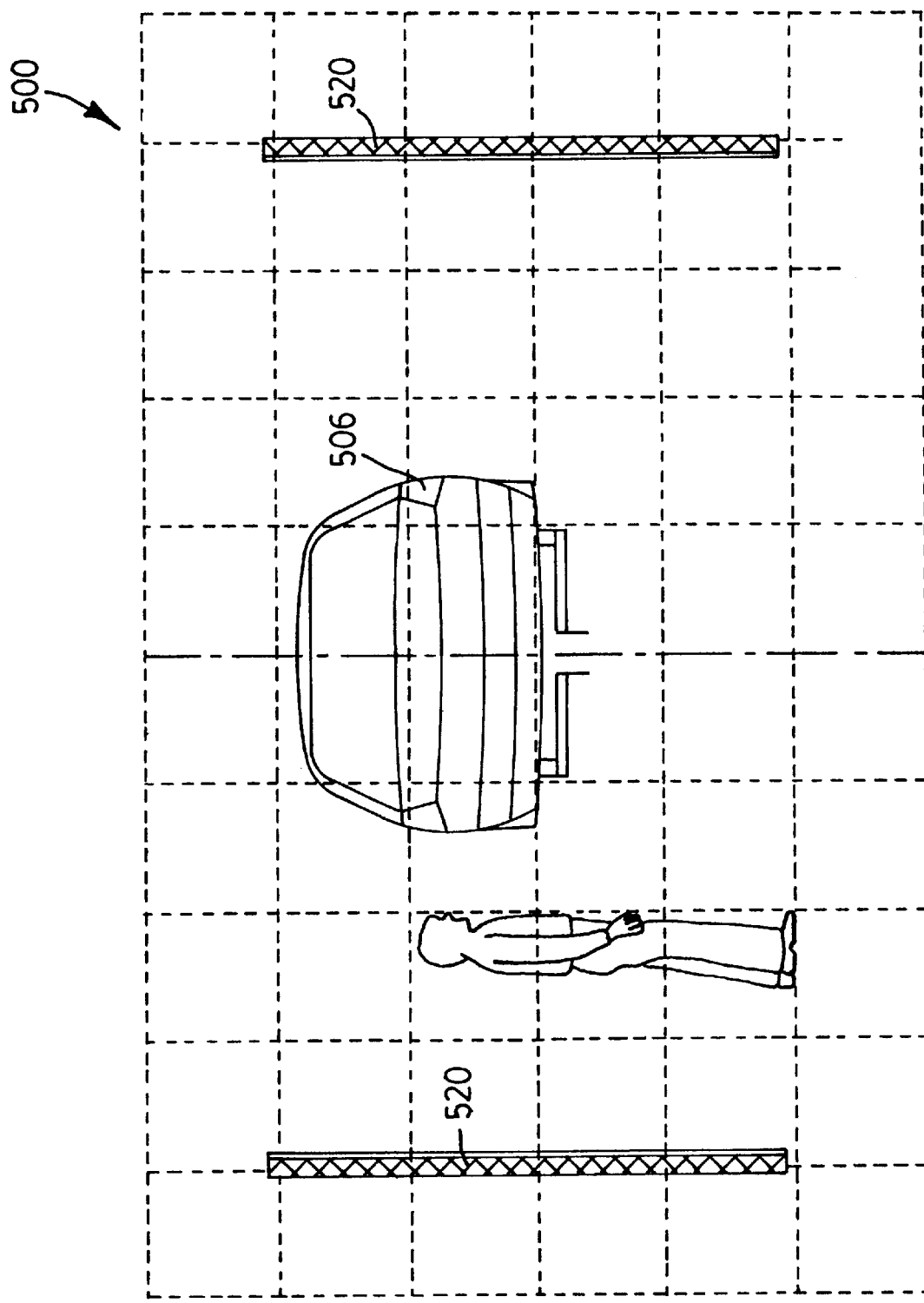

In the embodiment of FIG. 8c, the assembly line 506 is at eye level with respect to inspection personnel. In this case, only upright luminaires 520 are provided in the inspection area 500 on opposite sides of the assembly line.

Figure 8D:
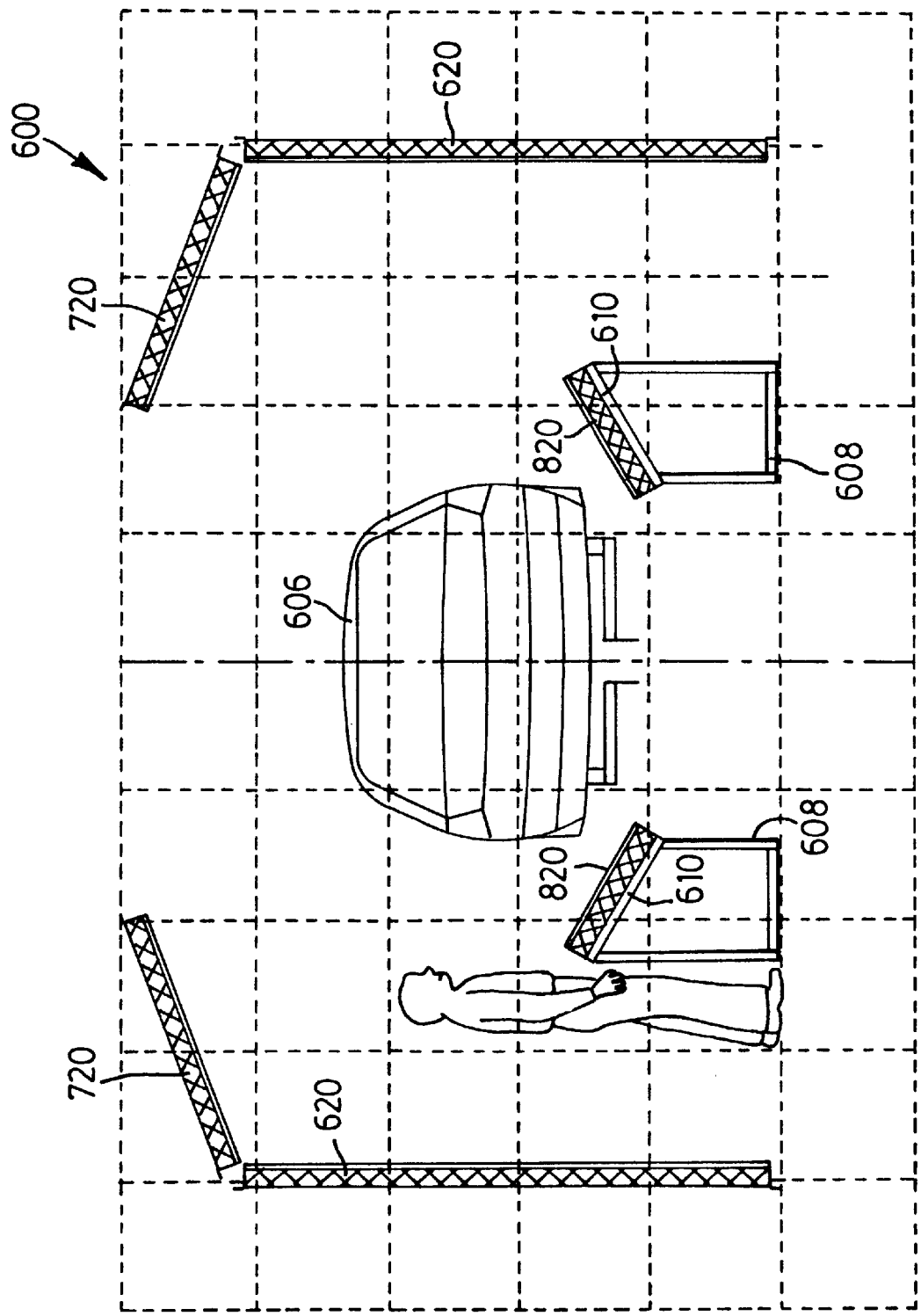

In the embodiment shown in FIG. 8d, the assembly line 606 is generally at waist level with respect to inspection personnel. In addition to the upright luminaires and smaller angled upper luminaires 620 and 720 respectively, the inspection area 600 includes small luminaires 820 mounted on supports 608 on opposite sides of the assembly line 606. The supports provide an inclined mounting surface 610 and are positioned slightly below the assembly line.

In the inspection areas shown in FIGS. 8a to 8d, the luminaires are positioned and oriented to limit the amount of bobbing and weaving inspection personnel must do to inspect visually the specular surfaces of the entire automobile while illuminating all specular surfaces visible to the inspection personnel.

As will be appreciated, the present inventions facilitates surface defect detection while maintaining illuminance at recommended levels. Although the linear reflectors have been described as being formed of aluminum, it should be appreciated by those of skill in the art that other highly reflective material can be used. Also, although each luminaire is shown to include a pair of fluorescent lamp assemblies, the number of fluorescent lamp assemblies is arbitrary and can be increased or decreased as desired.

Although the luminaires have been shown in an automobile assembly line, it will be appreciated by those of skill in the art that the luminaires may be used in virtually any environment where coated surfaces are to be inspected for defects.

Those of skill in the art will also appreciate that other variations and modifications may be made to the present invention without departing from the spirit and scope thereof as defined by the appended claims.

We claim:

1. A luminaire to illuminate an article to be visually inspected for defects, said luminaire and article being moved relative to one another, said luminaire comprising:

a housing having an opening in a face thereof directed towards the article being inspected;

at least one elongate light source accommodated within said housing; and at least one linear reflector within said housing and having at least one forwardly directed, angled reflective surface, said at least one reflective surface reflecting light emitted by said at least one elongate light source through said opening to illuminate a specular surface of said article being inspected as said article and luminaire move relative to one another, said at least one linear reflector being positioned relative to said at least one elongate light source such that sharp, laterally spaced linear edges of demarcation are visible on said specular surface as a result of said illumination, wherein defects in said article disrupt said linear edges as said article and luminaire move relative to one another thereby to enable defects to be visually detected.

2. The luminaire as defined in claim 1 further comprising a pair of linear reflectors associated with each said at least one elongate light source, the linear reflectors of said pair being located on opposite sides of said associated elongate light source.

3. The luminaire as defined in claim 2 wherein said linear reflectors are mounted on a rigid support, said support including a pair of diverging, forwardly extending panels positioned on opposite sides of said at least one elongate light source, said panels being joined by a generally planar, substantially non-reflective intermediate panel positioned behind said at least one elongate light source, each of said diverging panels presenting an angled, forwardly directed mounting surface on which said linear reflectors are mounted.

4. The luminaire as defined in claim 3 wherein said intermediate panel is coated with a black matte enamel.

5. The luminaire as defined in claim 4 wherein said diverging and intermediate panels are integrally formed.

6. A luminaire as defined in claim 4 wherein each of said diverging panels form an angle with said intermediate panel equal to approximately 130 degrees.

7. The luminaire as defined in claim 6 including a single elongate light source in the form of a low energy fluorescent lamp assembly.

8. The luminaire as defined in claim 3 wherein said linear reflectors are polished specular aluminum and are secured to said diverging panels via sheet adhesive.

9. The luminaire as defined in claim 8 wherein said linear reflectors have a reflectance equal to approximately 93%.

10. The luminaire as defined in claim 1 further comprising a clear lens on said housing and overlying said opening to seal said housing thereby to inhibit accumulation of foreign particulate matter on said at least one reflective surface and said light source.

11. The luminaire as defined in claim 10 wherein said housing has a volume selected to maintain a relatively constant temperature in said housing.

12. A luminaire to illuminate an article to be visually inspected for defects as said article and luminaire move relative to one another, said luminaire comprising:

a generally rectangular housing having an opening in a forward face thereof directed towards the article being inspected;

a pair of laterally spaced, fluorescent lamp assemblies within said housing, each fluorescent lamp assembly including an elongate fluorescent lamp; and a pair of linear reflectors within said housing associated with each fluorescent lamp assembly, the linear reflectors of each pair being located on opposite sides of said associated fluorescent lamp assembly and presenting angled, forwardly directed highly reflective surfaces, the reflective surfaces of each linear reflector reflecting light emitted by said associated fluorescent lamp assembly through said opening to illuminate a specular surface of said article being inspected as said article and luminaire move relative to one another, the linear reflectors of each pair being positioned with respect to the associated fluorescent lamp assembly and being supported within said housing such that sharp laterally spaced linear edges of demarcation are visible on said specular surface as a result of said illumination, wherein defects in said article disrupt said linear edges as said article and luminaire move relative to one another thereby to enable defects to be visually detected.

13. The luminaire as defined in claim 12 wherein the linear reflectors of each pair are mounted on a rigid support, each support including a pair of diverging panels bridged by an intermediate panel positioned directly behind said fluorescent lamp assembly, said intermediate panel presenting a forwardly directed, non-reflective surface.

14. A luminaire as defined in claim 13 wherein said diverging panels form an angle with said intermediate panel equal to approximately 130 degrees.

15. The luminaire as defined in claim 13 further comprising a clear lens on said housing and overlying said opening to seal said housing thereby to inhibit accumulation of foreign particulate matter on said reflective surfaces and said fluorescent lamps.

16. The luminaire as defined in claim 15 wherein said fluorescent lamps and the volume of said housing are selected to maintain a relatively constant temperature in said housing.

17. The luminaire as defined in claim 13 wherein said linear reflectors are polished specular aluminum and are secured to said diverging panels via sheet adhesive.

18. The luminaire as defined in claim 17 wherein said linear reflectors have a reflectance equal to approximately 93%.

19. An inspection area for an assembly line including a plurality of luminaires, said luminaires being positioned relative to said assembly line to illuminate specular surfaces of articles traveling along said assembly line, each of said luminaires comprising:

a housing having an opening in a face thereof directed towards said assembly line;

at least one fluorescent lamp assembly accommodated by said housing and including an elongate low energy fluorescent lamp; and at least one linear reflector within said housing and having at least one forwardly directed, angled highly reflective surface, said at least one reflecting surface reflecting light emitted by said at least one fluorescent lamp assembly through said opening, to illuminate a specular surface of said article being inspected as said article and luminaire move relative to one another, said at least one linear reflection being positioned with respect to the said at least one fluorescent lamp assembly such that sharp, laterally spaced linear edges of demarcation are visible on said specular surface as a result of said as a result of said illumination, wherein defects in said article disrupt said linear edges as said article and luminaire move relative to one another thereby to enable defects to be visually detected.

20. The inspection area as defined in claim 19 wherein said articles are in the form of automobiles.

21. An inspection area as defined in claim 20 wherein each of said luminaires includes a pair of fluorescent lamp assemblies and a pair of linear reflectors associated with each of said fluorescent lamp assemblies, the linear reflectors of said pair being located on opposite sides of said associated fluorescent lamp assembly and presenting angled, forwardly directed reflective surfaces.

22. An inspection area as defined in claim 21 wherein said linear reflectors of each pair are mounted on a rigid support, each support including a pair of diverging panels bridged by an intermediate panel positioned directly behind said fluorescent lamp assembly and presenting a forwardly directed non-reflective surface, said diverging panels forming angles with said intermediate panel equal to approximately 130 degrees.

23. An inspection area as defined in claim 22 wherein each of said luminaires includes a clear lens overlying said opening to seal said housing thereby to inhibit accumulation of foreign particulate matter on said reflective surfaces and fluorescent lamp.

24. The luminaire as defined in claim 23 wherein said linear reflectors are polished specular aluminum and are secured to said diverging panels via sheet adhesive.

25. The luminaire as defined in claim 24 wherein said linear reflectors have a reflectance equal to approximately 93%.

26. The luminaire as defined in claim 25 wherein said fluorescent lamps and the volume of said housing are selected to maintain a relatively constant temperature in said housing.

* * * * *